United States Patent [19]

Mallon

[11] Patent Number: 4,487,949

[45] Date of Patent: Dec. 11, 1984

[54] PROCESS FOR THE PREPARATION OF ALKYL SILICATES

[75] Inventor: Charles B. Mallon, Belle Mead, N.J.

[73] Assignee: Union Carbide Corporation, Danbury, Conn.

[21] Appl. No.: 554,292

[22] Filed: Nov. 22, 1983

[51] Int. Cl.³ ............... C07C 7/04; C07C 7/08; C07C 7/18

[52] U.S. Cl. .................... 556/470; 556/472

[58] Field of Search ........................ 556/470

[56] References Cited

U.S. PATENT DOCUMENTS

| | | | |
|---|---|---|---|
| 2,473,260 | 6/1949 | Rochow | 556/470 |
| 3,627,807 | 12/1971 | Bleh et al. | 556/470 |
| 4,288,604 | 9/1981 | Magee et al. | 556/470 |

FOREIGN PATENT DOCUMENTS

| | | | |
|---|---|---|---|
| 55-11538 | 1/1980 | Japan | 556/470 |
| 16492 | 2/1981 | Japan | 556/470 |

*Primary Examiner*—Paul F. Shaver
*Attorney, Agent, or Firm*—Bernard Francis Crowe

[57] ABSTRACT

Tetraalkyl orthosilicates may be prepared in good yield by contacting an alkanol having 1 to about 4 carbon atoms with copper-activated silicon synthesized by heating a mixture of cupric oxide and silicon particles at elevated temperatures at a temperature of about 120°–250° C. under autogeneous pressure.

11 Claims, No Drawings

PROCESS FOR THE PREPARATION OF ALKYL SILICATES

BACKGROUND OF THE INVENTION

This invention pertains to the preparation of alkyl silicates and more particularly to the use of silicon activated with cupric oxide.

BACKGROUND ART

Ethyl silicate is currently produced by reaction of silicon tetrachloride with ethanol. Although the chemistry of this process is very simple, it does have two significant disadvantages: the coproduction of copious amounts of hydrogen chloride, which necessitates the use of equipment made of expensive alloys and also presents disposal problems; and the cost of silicon tetrachloride.

A survey of the patent literature indicates that these deficiencies have been recognized by others as well. As long ago as 1949, a patent issued to Rochow (U.S. Pat. No. 2,473,260) describes a process for preparation of methyl silicate from methanol and silicon-copper masses. It is noted, however, that ethanol reacts so slowly that direct production of ethyl silicate is impractical.

Dynamit Nobel has done substantial work on a process for making silicates from silicon and alcohols in the presence of alkali methal alkoxide catalysts. As described in U.S. Pat. Nos. 3,557,179; 3,627,807; 4,113,761; and 4,185,029, this process is very useful for preparation of methyl silicate. Preparation of ethyl silicate is possible, however, if the reaction mixture contains some source of methoxy groups and surface active agents and the reaction is run at high temperature with very small particle size silicon (preferably 2–20 microns).

Patents assigned to Anderson Development Company (U.S. Pat. No. 3,803,197) and Stauffer Chemical Company (U.S. Pat. No. 4,288,604) describe a process for the preparation of ethyl silicate from ethanol and silicon in a high boiling alcohol solvent (e.g., butyl CARBITOL) in the presence of the alkali metal salt of the alcohol.

Another variation on the base catalyzed process has been patented by Carboline (U.S. Pat. No. 4,323,690). Here, the catalyst is a weak base, the alkali metal salt of a carboxylic acid (e.g., sodium formate). A detailed evaluation of this process led to the conclusion that substantial amounts of methanol were necessary for reasonable reaction rates in the process, leading to the production of methyl silicates, exposure to which could cause serious health problems.

Several Japanese patents and one U.S. Pat. No. (3,775,457) describe preparation of ethyl silicates from silicon and alcohols in the presence of cuprous chloride, nickel chloride, and/or combinations of these catalysts. These processes generally produce mixtures of the trialkoxy and tetraalkoxy silanes and have demonstrated very low reaction rates and yields.

Finally, U.S. Pat. No. 4,289,889 describes a process developed by W. B. Herdle and B. Kanner in which ethyl silicate is produced by reaction of a silicon-copper active mass with a mixture of ethanol and dimethylamine in a fluidized bed reaction. Reaction rates are high, yields are excellent and ethyl silicate is the only isolated product. This process requires a fluidized bed reactor, dimethylamine handling and recycle system, active mass preparation and storage system.

In view of the amount of technology that has been developed on silicon metal based processes, it is surprising that until recently all domestic ethyl silicate was being prepared from silicon tetrachloride. This may be partially due to a number of factors, including the complexity and difficulty of running the silicon metal based processes, and the inability of most of the processes to make ethyl silicates directly at practical rates of reaction.

It is, therefore, an object of this invention to provide a simpler method for preparing alkyl silicates than is presently available.

It is another object of this invention to prepare alkyl silicates in good yield from an alkanol and silicon metal which has been activated.

Other objects will become apparent to those skilled in the art upon a further reading of the specification.

DISCLOSURE OF THE INVENTION

A method has been found for synthesizing tetraalkyl orthosilicates which comprises the steps of:

(A) calcining a mixture of cupric oxide and silicon particles containing about 1 to about 10 weight percent of cupric oxide at a temperature of about 400°–1,000° C. for at least about 0.5 hours under an inert gas atmosphere; and (B) contacting the mixture treated in step (A) with a stoichiometric excess of an alkanol, having one to about four carbons, based on the weight of silicon in said mixture, at a temperature of about 120°–250° C. until a tetraalkyl silicate is obtained.

Any suitable inert gas can be used as for example, nitrogen, argon, helium, krypton, and the like.

Although the mixture of cupric oxide and silicon can contain about 1 to about 10 percent by weight of cupric oxide, it is preferred to use about 2 to about 8% and even more preferred to use about 3 to about 7%.

Without wishing to be bound or limited by theoretical explanations, it is believed that the compound responsible for activating the silicon so that it may react directly with an alkanol, is actually cuprous oxide. This is believed to be generated when cupric oxide-silicon mixtures are heated at elevated temperatures. It is also not necessary that pure cupric oxide be used in this invention for providing an activated silicon. Thus, for example, one may employ comparable amounts of cement copper which is a trade designation for a relatively poorly defined mixture of copper metal, and cuprous and cupric oxides. This is believed to be due to the fact that the conversion of cupric oxide to cuprous oxide is known to occur under the conditions used to prepare the activated silicon. In this regard, temperatures of about 500°–700° C. are preferred in calcining the cupric oxide-silicon mixture, although temperatures of about 400° to about 1,000° C. can also be used.

Pressure is not narrowly critical. The reaction is usually conducted at the autogeneous pressure developed in the closed reactor due to the vapor pressure of the particular alkanol employed.

The particle size of the silicon used, however, is critical inasmuch as this factor affects the yield of tetraalkyl orthosilicate obtained. It has been found that silicon particles larger than −325 mesh or 44 microns cause a diminution in the yield. Thus, although silicon particles in the range of 60–150 mesh produce tetraalkyl orthosilicates, the yield is lower.

Suitable alkanols for use in the claimed process include methanol, ethanol, n-propanol, n-butanol, and the like.

The temperature of the reaction between these alkanols and the activated silicon particles is preferably held between 170° and 190° C., although temperatures of about 120° to about 250° C. can be used. Temperatures below this range result in a falling off of the yield of tetraalkyl orthosilicate.

While pressure equipment is required for the practice of this invention, it is equipment known to those skilled in the art and no special description is needed.

The invention is further described in the Examples which follow. All parts and percentages are by weight unless otherwise specified.

The silicon used in the examples was purchased from Alfa Products and is claimed to be at least 99.5% pure on a metals basis.

Anhydrous grade alkanols were used in all cases.

PREPARATION OF ACTIVATED SILICON

The desired proportions of cupric oxide or cement copper and particulate silicon were first mixed with a mortar and pestle and then transferred to ceramic boats. These boats were heated or calcined in a tubular furnace at the desired temperatures under a flow of nitrogen for activation.

GENERAL EXPERIMENTAL PROCEDURE

All reactions were performed in a 1 liter stainless steel pressure reactor equipped with a pitched blade turbine agitator, electric heaters, cooling coils, vent valve, and nitrogen purge inlet. The silicon and alcohols (350 g–500 g total) were charged to the reactor and the head was bolted on. The agitation speed was set at 1500 rpm and a slow flow of nitrogen was passed through the reactor for 15 minutes. All valves were then closed, the heaters turned on, and the temperatures setpoint set to 180° C. Temperature and pressure were monitored and recorded at appropriate times and the reactor was vented as the pressure reached 700 psig, reducing it to about 400 psig. This was continued for 3.5–4.5 hours, by which time no further pressure increases could be observed, and then the reactor contents were cooled and removed for analysis. Gas chromatography, using hexadecane as an internal standard, was used to determine the amount of silicates produced.

Control A

In order to demonstrate that the mere presence of copper, not cupric oxide, in a reaction mixture is not sufficient to effect the reaction mixture is not sufficient to effect the reaction between silicon and an alkanol, an experiment was conducted in which 500 g of ethanol and 30 g of highly purified silicon (finer than 100 mesh) were reacted as in Examples 1–10 in the presence of cuprous chloride. This experiment resulted in the production of only a trace of tetraethyl orthosilicate, approximately 0.01 mole, or approximately 20 to 30 times less than that produced using the cupric oxide activated silicon described above.

Control B and Control C

In order to compare the present invention with the prior art, two experiments were carried out in accordance with the teachings of U.S. Pat. No. 4,323,690. In the first experiment, 414 g of ethanol and 64 g of silicon (<100 mesh) were reacted as described in Examples 1–6 at temperatures up to 200° C. using 22 g of potassium formate as catalyst. After a reaction time of 3.5 hours, examination of the liquid phase by gas chromatography indicated that essentially no tetraethyl orthosilicate had been produced.

A second experiment employed 47 g of silicon (−100 mesh) at 200° C. for 3.5 hours with 250 g each of methanol and ethanol in the presence of 6.6 g of sodium formate as catalyst. This reaction produced 0.32 mole of a mixture of orthomethyl and orthoethyl silicates. These results demonstrate that the alkali metal formate catalyzed reaction of alkanols with silicon is extremely sensitive to the identity of the alkanol, being quite productive when a large proportion of methanol is used but producing virtually no silicate when the alkanol component is pure ethanol. This is in sharp contrast to the present invention where reactions with methanol, ethanol, n-propanol, and n-butanol have all been demonstrated to proceed with cupric oxide activated silicon.

EXAMPLES 1–10

A series of experiments was run with 350 g of ethanol using the general experimental procedure described above. The activated silicon was made from cement copper (a mixture of cuprous oxide, cupric oxide and metallic copper) mixed with small size silicon particles (−325 mesh, 44 micron maximum). The results of these reactions are summarized in Table 1.

EXAMPLE 11

A run was made to determine the lowest temperature at which some reaction between copper activated silicon and ethanol could be detected. The reaction was run as described above with 30 g of Si/CuO and 500 g of ethanol but the temperature was adjusted at various times to determine where the reaction stops. It was found that little or no reaction was detectable at 110° C., but pressure began to increase at 120° C. due to the generation of hydrogen gas, indicating that the reaction was occurring at this temperature.

TABLE 1

| Example | Activated Si[1] Wt. % Cement Copper | Preparation Conditions Calcination Time | Temp. | Si Charged | Si Consumed | Tetraethyl Silicate Produced | Yield[2] |
|---|---|---|---|---|---|---|---|
| 1 | 5 | 2.5 hrs. | 500° C. | 333 mmol | 210 mmol, 63% | 155 mmol | 47% |
| 2 | 5 | 3 hrs. | 500° C. | 333 mmol | 285 mmol, 86% | 278 mmol | 83% |
| 3 | 5 | 16 hrs. | 500° C. | 333 mmol | 217 mmol, 65% | 133 mmol | 40% |
| 4 | 20 | 2 hrs. | 500° C. | 286 mmol | 183 mmol, 64% | 166 mmol | 58% |
| 5 | 5 | 0.5 hrs. | 300° C. | 333 mmol | 92 mmol, 28% | 1 mmol | 0.3% |
| 6 | 5 | 7 hrs. | 300° C. | 333 mmol | 92 mmol, 28% | 1 mmol | 0.3% |
| 7 | 5 | 0.5 hrs. | 400° C. | 333 mmol | 210 mmol, 63% | 165 mmol | 50% |
| 8 | 5 | 0.5 hrs. | 700° C. | 333 mmol | 293 mmol, 88% | 246 mmol | 74% |
| 9 | 5 | 2 hrs. | 700° C. | 333 mmol | 280 mmol, 84% | 285 mmol | 86% |

TABLE 1-continued

| Example | Activated Si[1] Wt. % Cement Copper | Preparation Conditions Calcination Time | Temp. | Si Charged | Si Consumed | Tetraethyl Silicate Produced | Yield[2] |
|---|---|---|---|---|---|---|---|
| 10 | 5 | 0.5 hrs. | 900° C. | 333 mmol | 149 mmol, 45% | 108 mmol | 32% |

[1]The silicon was purchased from Alfa Products.
[2]Yield is calculated as moles of tetraethyl orthosilicate produced per mole of silicon charged.

TABLE 2

| Example | Activated Si[1] Metal Source, Wt. % | Preparation Conditions Calcination Time | Temp. | Si Charged | Si Consumed | Tetraethyl Orthosilicate Produced | Yield[2] |
|---|---|---|---|---|---|---|---|
| 12 | CuCl, 7 | 4 hrs. | 500° C. | 333 mmol | 117 mmol, 35% | 62 mmol | 18% |
| 13 | Cu, 5 | 0.5 hrs. | 700° C. | 333 mmol | 48 mmol, 14% | 3 mmol | 1% |
| 14 | Ni, 5 | 0.5 hrs. | 700° C. | 333 mmol | 40 mmol, 12% | 0 mmol | 0% |
| 15 | NiCl$_2$ | 10 hrs. | 700° C. | 333 mmol | 50 mmol, 15% | 1 mmol | 0.3% |
| 16 | Cement Copper, 5 Ni, 2 | 0.5 hrs. | 700° C. | 333 mmol | 217 mmol, 65% | 175 mmol | 53% |
| 17 | CuO, 10 | 0.5 hrs. | 700° C. | 333 mmol | 261 mmol, 78% | 254 mmol | 76% |
| 18 | CuO, 1 | 0.5 hrs. | 700° C. | 333 mmol | 100 mmol, 30% | 51 mmol | 15% |
| 19 | CuO, 5 | 0.5 hrs. | 700° C. | 333 mmol | 258 mmol, 70% | 261 mmol | 78% |

[1]Silicon was purchased from Alfa Products (−325 mesh). P.O. Box 299, 152 Andover Street, Danvers, Massachusetts 01923. The minus sign (−) means all the particles are smaller than 44 microns, the sieve opening size.
[2]Yield is calculated as moles of silicate produced per mole of silicon consumed.

Examination of the data presented in Table 1 leads to the following conclusions:

(1) Calcination temperatures below about 400° C. afford activated silicon mixtures of low activity;

(2) Silicon mixtures prepared with 5% and 20% cement copper display similar activities for the preparation of tetraethyl orthosilicate;

(3) Optimum temperatures for preparation of activated silicon mixtures are 700° C. for 0.5 hours; and (4) Consistent yields of about 80% overall are obtainable with this invention.

Since cement copper is relatively poorly defined mixture of copper metal and cuprous and cupric oxides, it was decided to investigate the activating effectiveness of copper in each valence state and of another metal, nickel, often mentioned as a silicon activator. This series of reactions summarized in Table 2 was run following the procedure described in Examples 1–10.

In examining the yields of tetraethyl orthosilicate in the reactions, it is immediately apparent that the only species with an activating efficiency close to that of cement copper is cupric oxide. At levels of 5% and 10% relative to silicon, a mass is formed that produces 78% and 76% ethyl silicate, respectively. At a 1% level, the yield drops to 15%.

Although the invention has been described in its preferred forms with a certain degree of particularity, it is understood that the present disclosure has been made only by way of example and that numerous changes can be made without departing from the spirit and scope of the invention.

I claim:

1. Method of synthesizing tetraalkyl orthosilicates which comprises the steps of:
   (A) calcining a mixture of cupric oxide and silicon particles containing about 1 to about 10 weight percent of cupric oxide at a temperature of about 400°–1,000° C. for at least about 0.5 hours under an inert gas atmosphere; and
   (B) contacting the mixture treated in step (A) with a stoichiometric excess of an alkanol, having one to about four carbons, based on the weight of silicon in said mixture, at a temperature of about 120°–250° C. until a tetraalkyl silicate is obtained.

2. Method claimed in claim 1 wherein the cupric oxide is introduced in step (A) as cement copper.

3. Method claimed in claim 1 wherein the cupric oxide is introduced in step (A) contains about 2 to about 8% cupric oxide.

4. Method claimed in claim 1 wherein the mixture in step (A) contains about 5 to about 10% cupric oxide.

5. Method claimed in claim 1 wherein the alkanol in step (B) is ethanol.

6. Method claimed in claim 1 wherein the alkanol in step (B) is methanol.

7. Method claimed in claim 1 wherein the alkanol in step (B) is n-propanol.

8. Method claimed in claim 1 wherein the alkanol in step (B) is n-butanol.

9. Method claimed in claim 1 wherein the temperature is about 170° to about 190° C.

10. Method claimed in claim 1 wherein the inert gas atmosphere is nitrogen.

11. Method claimed in claim 1 wherein the temperature is about 500° to about 700° C.

* * * * *